United States Patent [19]

Ron et al.

[11] Patent Number: 5,122,367
[45] Date of Patent: Jun. 16, 1992

[54] POLYANHYDRIDE BIOERODIBLE CONTROLLED RELEASE IMPLANTS FOR ADMINISTRATION OF STABILIZED GROWTH HORMONE

[75] Inventors: Eyal Ron, Lexington, Mass.; Mark Chasin, Englishtown, N.J.; Tom Turek, Dorchester; Robert S. Langer, Newton, both of Mass.

[73] Assignees: Massachusetts Institute of Technology, Cambridge, Mass.; Nova Pharmaceutical Corporation, Baltimore, Md.

[21] Appl. No.: 332,554

[22] Filed: Mar. 31, 1989

[51] Int. Cl.$^5$ .............................................. A61K 31/74
[52] U.S. Cl. ....................................... 424/80; 424/78; 424/81; 424/426
[58] Field of Search ................... 424/78, 80, 426, 81

[56] References Cited

U.S. PATENT DOCUMENTS

| | | |
|---|---|---|
| 3,993,071 | 11/1976 | Higuchi et al. |
| 4,638,045 | 1/1987 | Kohn et al. |
| 4,657,543 | 4/1987 | Langer et al. ..................... 424/486 |
| 4,675,189 | 6/1987 | Kent et al. ..................... 424/426 |
| 4,708,861 | 11/1987 | Popescu et al. ..................... 424/458 |
| 4,745,160 | 5/1988 | Churchill et al. ..................... 525/415 |

OTHER PUBLICATIONS

Leong et al., *J. Biomed. Mater. Res.*, 19, 941–955 (1985).
Leong et al., *Macromolecules* 20, 705–712 (1987).
Mathiowitz et al., *Proc. Intl. Symp. Con. Release Bioactive Mat.* 12, 183–184 (1985).
Mathiowitz et al., *J. Controlled Release* 5, 13–22 (1987).
Rosen et al., *Biomaterials* 4, 131–133 (1983).

*Primary Examiner*—Thurman K. Page
*Assistant Examiner*—Peter F. Kulkosky
*Attorney, Agent, or Firm*—Kilpatrick & Cody

[57] ABSTRACT

A controlled release device for the administration of biologically active growth hormone proteins or peptide fragments, and method of preparation thereof, wherein biologically active growth hormone is stabilized and release rate modulated by incorporation of a stabilizing compound. The controlled release devices are prepared by mixing a stabilizer, such as sucrose, with a biologically active growth hormone, such as bovine somatotropic hormone, in solution, lyophilizing, then incorporating the dried powder into a surface erodible, biocompatible polymeric matrix, such as a poly(anhydride) or poly(orthoester) matrix.

11 Claims, 2 Drawing Sheets

POLYANHYDRIDE BIOERODIBLE CONTROLLED RELEASE IMPLANTS FOR ADMINISTRATION OF STABILIZED GROWTH HORMONE

BACKGROUND OF THE INVENTION

A method and device generally in the area of bioerodible controlled release systems for the delivery and administration of biologically active growth hormone.

The concept of using biodegradable polymeric matrix systems for the delivery and controlled release of drugs and therapeutically active agents has only recently been developed and demonstrated to be clinically useful. Active agents have conventionally been administered by the periodic application of dosages in the form of injections, pills, liquids or topical treatments such as ointments, creams, or sprays. Drugs administered by these methods are generally neither confined to the target area nor delivered in a linear, continuous manner. The result is evident in the variable levels of active agent both above and below the efficacy level, physical discomfort and expense in the case of repeated subcutaneous injections, and inconvenience due to the requirement of timely applications. The efficacy of treatment may also be compromised as a result of failure to fulfill the prescribed treatment regime due to negligence, lapse, or non-compliance.

Alternative methods of delivery which correct these deficiencies have been sought for years. Bioerodible polymeric matrix compositions hold much promise in the development of improved delivery systems. Several polymers have been used for this application, including poly(anhydrides), poly(lactic acid), poly(orthoesters), and ethylene vinyl acetate. Poly(anhydrides) have been found to produce superior release when linear, or zero order, release rates are desirable, using shapes that do not significantly change their surface area as a function of time.

An example of a biologically useful protein that is most effective when delivered continuously over extended periods of time is growth hormone. Unfortunately, this protein frequently aggregates and loses activity, making it difficult to deliver on a continuous basis.

A controlled release polymer implant system that has been developed to deliver growth hormone is described in European Patent Application No. 86305431.8. This system, however, has several drawbacks. For example, because the device is not biodegradable, the device must be removed after treatment. Furthermore, the polymer utilized to form the device is limited to those which do not bind to nor promote aggregation of the growth hormone. This limitation in the choice of the polymer also limits the range and extent of release of active agent. Polymers which might otherwise be desirable for reasons of release kinetics and duration, specifically polymers that are more hydrophilic or more hydrophobic in nature, cannot be used due to interactions with, or adverse influence upon, the active agent. The device is also limited to subcutaneous implantation in animals since use in humans would require post-treatment removal of the device.

It is therefore an object of the present invention to provide a biodegradable controlled release implantable device for controlled in vivo administration of growth hormone.

It is a further object of the present invention to provide a method and means for the stabilization of growth hormone in bioerodible polymeric matrices.

It is a still further object of the present invention to provide a method and means for modulating the rate of release of the stabilized polypeptidic agents from the bioerodible polymeric matrix.

SUMMARY OF THE INVENTION

An improved surface erodible controlled release composition for the continuous administration of biologically active growth hormone proteins or peptide fragments, and a method for the manufacture thereof. The biologically active growth hormone is first combined with a stabilizing agent in solution, then the combination dried to a powder. The dried mixture is subsequently incorporated into a polymeric matrix formed from a surface erodible, biocompatible polymer such as a poly(anhydride) or poly(orthoester).

In the preferred embodiment, a simple polysaccharide such as sucrose is used both as a stabilizer, to hinder denaturation and to increase the thermal stability of the growth hormone, and to modulate the release rate of the growth hormone from the bioerodible controlled release device. The result is an increase in the duration of release of the peptide and a decrease in initial release rate, when compared to non-stabilized composition, which permits longer and more uniform therapeutic treatment, without aggregation of the growth hormone.

BRIEF DESCRIPTION OF THE DRAWINGS

FIG. 1 are graphs of the percent cumulative release of bovine somatotropin (b-STH) as a function of time in hours, comparing release of unstabilized b-STH ( •—• ) (closed circles) with release of sucrose stabilized b-STH ( o—o ) (open circles).

DETAILED DESCRIPTION OF THE INVENTION

Figure 1A:
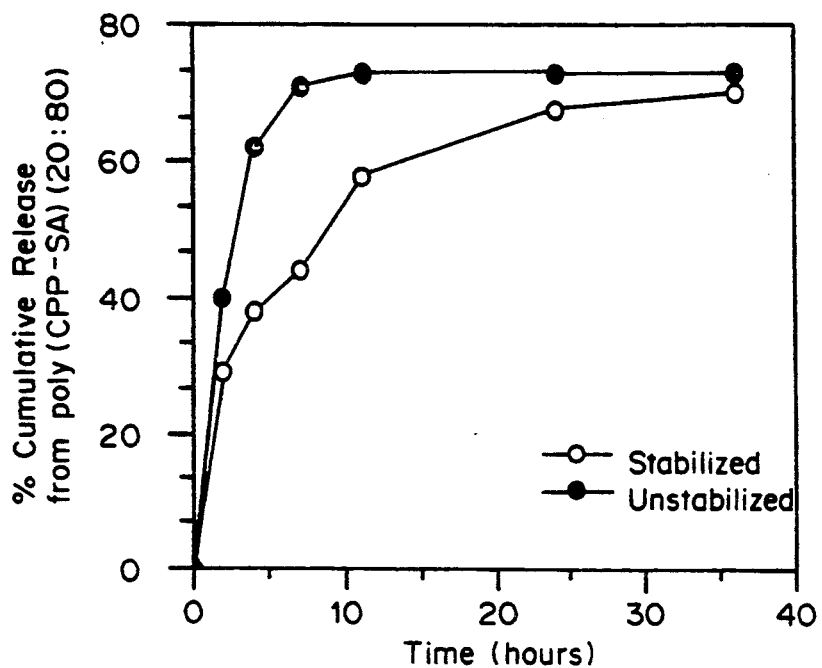
FIG. 1A compares release in poly(CPP:SA) (20:80) devices.

Controlled release compositions suitable for use in continuously delivering biologically active growth hormone, or somatotropin, having enhanced stability, with little or no aggregation, are provided.

The devices containing stabilized growth hormone are useful in a wide range of applications. Examples of specific applications where controlled and/or enhanced release is required include administration of growth hormones in livestock for increased milk production in lactating females and increased growth in maturing animals and administration of growth hormone in human patients.

The present invention is described in detail using bioerodible, biocompatible controlled release implants wherein the stabilized peptide is bovine somatotropic hormone (b-STH). However, any growth hormone-like protein or peptide having therapeutic or biological activity and physical and chemical properties similar to that of somatotropic hormone can be used in the present invention. The term "biologically active protein" refers to any therapeutically or biologically active protein, protein fragment, peptide, or analog thereof, unless otherwise stated, including proteins, active protein fragments and peptides which are naturally occurring, recombinantly engineered or synthetically produced and which may further undergo various modifications, such as additions to or deletions of amino acids or domains.

According to the method of the present invention, the biologically active growth hormone is co-lyophilized in the presence of a stabilizing compound such as, but not limited to, simple polysaccharides, including sucrose, glucose and fructose, polyhydric alcohols, and other protein stabilizing agents known to those skilled in the art. The preferred agent is sucrose.

The stabilizing agent has two effects on the growth hormone. It stabilizes and protects the growth hormone from degradation, thereby enhancing in vivo activity and allowing longer treatment periods before replacement of the implant. The addition and colyophilization of the stabilizing compound with the growth hormone also alters both the rate of release and duration of release of the growth hormone from the polymeric matrix. Significantly greater control of the release rate and released activity is achieved by this combination of stabilizer, growth hormone, and polymeric matrix.

The stabilized growth hormone is incorporated into a surface erodible, biocompatible polymeric matrix formed from surface eroding polymers such as poly(anhydrides) and poly(orthoesters). The more hydrophobic polymers are preferred. The use of a bioerodible polymeric matrix eliminates the need for post-treatment removal of the device and allows for more complete release of growth hormone. The controlled delivery device can be made according to several embodiments. In the preferred embodiment, the polymeric delivery device is formed from hydrophobic poly(anhydrides) and the stabilized growth hormone is uniformly distributed throughout the polymeric matrix. In another embodiment, the stabilized composition is encapsulated within microspheres.

The preferred method for making a stabilized biologically active growth hormone containing bioerodible controlled release device is as follows:

A biologically active growth hormone-like protein, as defined above, is mixed with a stabilizing agent, such as sucrose, in a ratio in the range of approximately one part peptide to two parts stabilizer to one part peptide to eight parts stabilizer. Approximately 120 mg to 360 mg of this mixture is added to 75 ml of highly purified water. This solution is then transferred to a 300 ml lyophilization flask. The solution is pre-frozen and lyophilized by standard methods. The resulting white crystalline powder is sieved, for example, to 250 $\mu$m, then dry mixed with the appropriate bioerodible and biocompatible polymer, such as a poly(anhydride) or poly(orthoester), at the desired loading ratio and processed by microencapsulation or pressing into the final product. The devices are preferably stored at $-20°$ C. under an argon atmosphere prior to use.

Poly(anhydrides) are used to form the polymeric matrix in the preferred embodiment. Unlike the devices described in European Patent Application 86305431.1, any biologically active growth hormone which has aggregated or bound to the polymer is only temporarily trapped within the device and is released during dispersion of the device. Non-bioerodible polymeric matrices not only must be removed post-treatment, but the active agent, in order to be released, must not aggregate nor bind to or otherwise interact with the polymer. Non-surface erodible polymers do not appear to effect release in the same way as the surface erodible polymers.

The present invention is further described with reference to the following non-limiting examples.

EXAMPLE 1

Preparation of Stable b-STH Composition for Enhanced Release from a p(CPP:SA) (20:80) device A bovine growth hormone composition was prepared by combining

| Bovine somatotropic hormone (b-STH) | 40 mg |
| Sucrose stabilizer | 80 mg to 320 mg |
| Poly (1,3-bis (p-carboxyphenoxy) propane - co - sebacic anhydride poly(CPP:SA) (20:80) | 95% (w/w) |

The b-STH and sucrose were mixed in solution and colyophilized as detailed above. The resulting powder was triturated with poly(CPP:SA) (20:80) and the mixture compression molded in a Carver press at 10,000 lbs. into a 150 mm diameter, 0.5 mm thick device weighing 200 mg.

Release of the b-STH from the device was measured in phosphate buffer, pH 7.4, over a period of forty hours. The results comparing release of the stabilized b-STH with unstabilized b-STH from the device are shown in FIG. 1A.

EXAMPLE 2

Preparation of Stable b-STH Composition for Enhanced Release from a p(CPP:SA) (50:50) device A bovine growth hormone composition was prepared by combining

| b-STH | 40 mg |
| Sucrose stabilizer | 80 mg to 320 mg |
| poly(CPP:SA) (50:50) | 95% (w/w) |

The b-STH and sucrose stabilizer were mixed in solution and co-lyophilized as detailed above. The resulting powder was mixed with poly(CPP:SA) (50:50) to a final ratio of 5% (w/w) b-STH/poly (CPP:SA) (50:50) and the mixture compression moulded in a Carver press at 10,000 lbs. into 150 mm diameter, 0.5 mm thick devices weighing 200 mg.

Figure 1B:
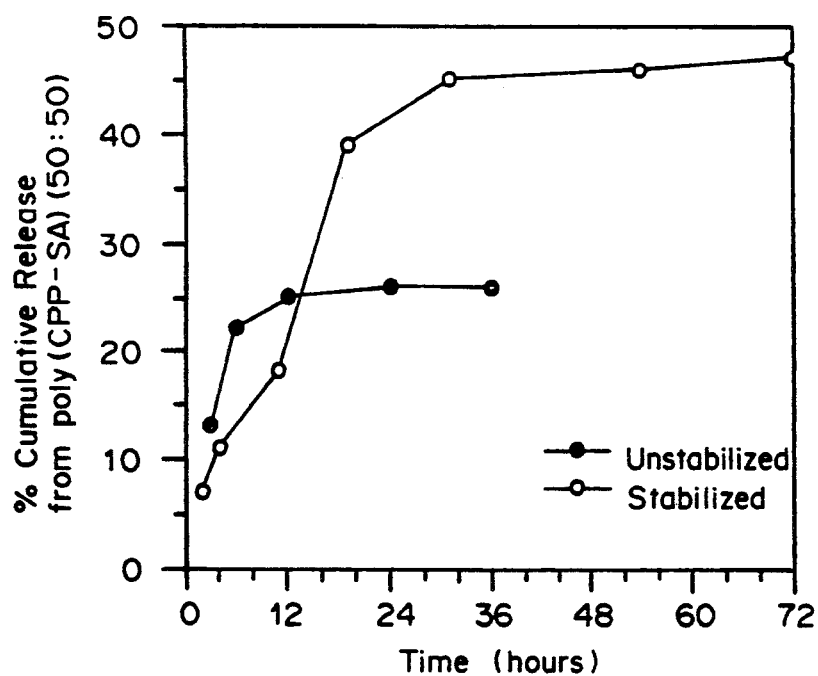
FIG. 1B compares release in poly(CPP:SA) (50:50) devices.

Release of the b-STH from the device was measured in phosphate buffer, pH 7.4, over a period of 72 hrs. The results comparing release of the stabilized b-STH with unstabilized b-STH from the device is shown in FIG. 1B.

In both examples 1 and 2, more of the stabilized growth hormone is released than of the unstabilized growth hormone (approximately 75% versus 55% at 10 hours for CPP:SA, 20:80, and 45% versus 25% at 30 hours for CPP:SA, 50:50). Further, the rate of release of the stabilized growth hormone is more linear than the rate of release of the unstabilized growth hormone.

EXAMPLE 3

Preparation of Stable b(STH) Composition for Enhanced Release from a p(CPH:SA) (50:50) device A bovine growth hormone composition is prepared by combining

| b-STH | 40 mg |
|---|---|
| Sucrose stabilizer | 80 mg to 320 mg |
| poly(CPH) | 95% (w/w) |

The b-STH and sucrose stabilizer were mixed in solution and co-lyophilized as detailed above. The resulting powder was mixed with poly(CPH) and the mixture compression moulded in a Carver press at 10,000 lbs. into 150 mm diameter, 0.5 mm thick devices weighing 200 mg.

Figure 2:
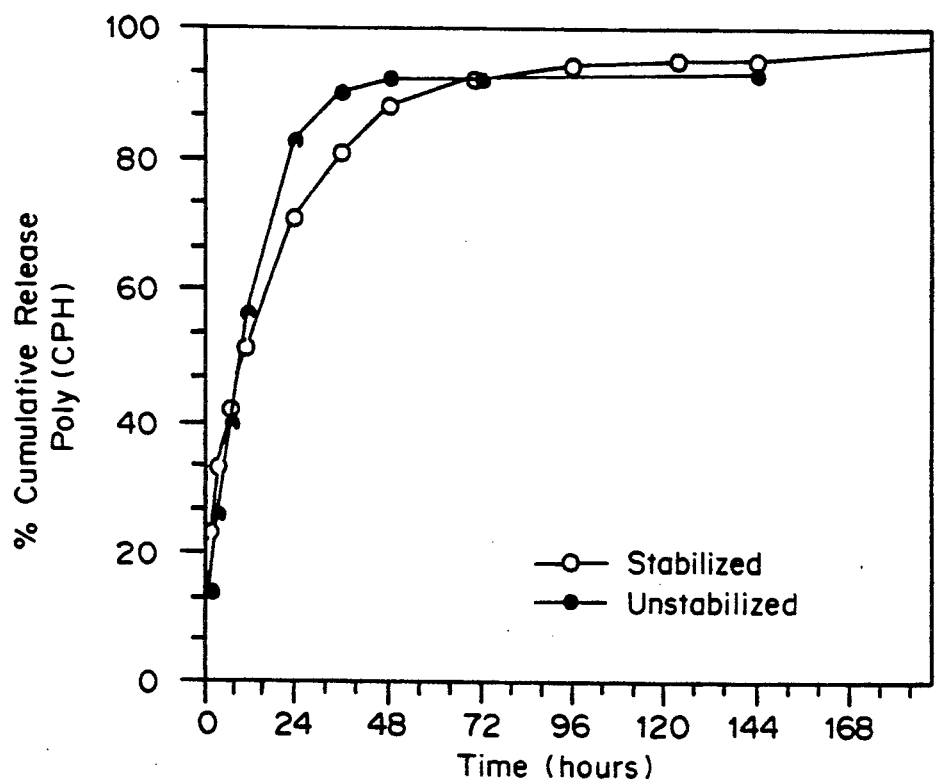
FIG. 2 is a graph of percent cumulative release of b-STH as a function of time in hours, comparing release of unstabilized b-STH ( •—• ) (closed circles) with release of sucrose stabilized b-STH ( o—o ) (open circles) in bioerodible poly(CPH) devices.

Release of the b-STH from the device was measured in phosphate buffer, pH 7.4, over a period of 168 hrs. The results comparing release of the stabilized b-STH with unstabilized b-STH from the device is shown in FIG. 2.

The results in the examples demonstrate that the combination of stabilizer and surface eroding matrix effects more complete release of growth hormone over an extended period of time. The highest yield and most linear results are obtained using more hydrophobic polymers such as poly(CPH) and poly(CPP:SA)(50:50).

Modifications and variations of the present invention, a bioerodible controlled release device containing a stabilized biologically active agent will be apparent to those skilled in the art from the foregoing detailed description of the invention such modifications and variations are intended to come within the scope of the appended claims.

We claim:

1. A controlled release system for a protein comprising:
   a protein having physical, chemical and biological activity equivalent to that of somatotrophin;
   a simple polysaccharide; and
   a biocompatible, surface erodible, hydrophobic polymeric matrix selected from the group consisting of polyanhydrides, poly(orthoesters), copolymers and combinations thereof, wherein the polysaccharide and protein are incorporated within and released from the polymeric matrix, the ratio of polysaccharide to protein in the matrix is greater than 1:1, and the rate of release of the protein in combination with the polysaccharide is more linear than the rate or release of the protein in the absence of the polysaccharide.

2. The controlled release system of claim 1 wherein the protein is elected from the group consisting of polypeptides, peptide fragments and natural, recombinant and synthetic analogs thereof of somatotrophin, having somatotrophin activity.

3. The controlled release system of claim 1 wherein the polysaccharide is selected from the group consisting of sucrose, glucose, and fructose.

4. The controlled release system of claim 1 wherein the polysaccharide is sucrose, the growth hormone like protein is biologically active growth hormone, and the polymeric matrix is formed from poly(anhydrides).

5. A method for making a delivery system for a protein comprising providing a protein having physical, chemical and biological activity equivalent to that of somatotrophin in combination with a simple polysaccharide and incorporating the combination within a biocompatible, surface erodible, hydrophobic polymeric matrix selected from the group consisting of polyanhydrides, poly(orthoesters), copolymers and combinations thereof, wherein the polysaccharide and protein are incorporated within and released from the polymeric matrix, the ratio of polysaccharide to protein is greater than 1:1 and the rate of release of the protein in combination with the polysaccharide is more linear than the rate of release of the protein in the absence of the polysaccharide.

6. The method of claim 5 further comprising lyophilizing a solution containing the protein and polysaccharide before incorporation into the polymer matrix.

7. The method of claim 5 wherein the polysaccharide is selected from the group consisting of sucrose, glucose, and fructose.

8. The method of claim 5 wherein the protein is selected from the group consisting of polypeptides, peptide fragments and natural, recombinant and synthetic analogs thereof of somatotrophin, having somatotrophin activity.

9. The method of claim 5 wherein the polysaccharide is sucrose, the growth hormone-like protein is biologically active growth hormone, and the polymeric matrix is formed from poly(anhydrides).

10. The delivery system of claim 1 wherein the polysaccharide to protein ratio is between approximately 2:1 and 8:1.

11. The method of claim 5 wherein the polysaccharide to protein ratio is between approximately 2:1 and 8:1.

* * * * *